United States Patent [19]
Thieme et al.

[11] Patent Number: 5,339,829
[45] Date of Patent: * Aug. 23, 1994

[54] ORAL COLLECTION DEVICE

[75] Inventors: Thomas R. Thieme, Independence; Andrew S. Goldstein; Stephen C. Piacentini, both of Portland; Nanette M. Klimkow, Beaverton, all of Oreg.

[73] Assignee: Epitope, Inc., Beaverton, Oreg.

[*] Notice: The portion of the term of this patent subsequent to Apr. 14, 2009 has been disclaimed.

[21] Appl. No.: 935,845

[22] Filed: Aug. 25, 1992

Related U.S. Application Data

[63] Continuation-in-part of Ser. No. 865,054, Apr. 8, 1992, abandoned, which is a continuation of Ser. No. 641,739, Jan. 15, 1991, Pat. No. 5,103,836, which is a continuation-in-part of Ser. No. 486,415, Feb. 28, 1990, abandoned, which is a continuation-in-part of Ser. No. 410,401, Sep. 21, 1989, Pat. No. 5,022,409.

[51] Int. Cl.$^5$ ............................................. A61B 5/00
[52] U.S. Cl. .................................... 128/760; 128/771
[58] Field of Search ............ 128/760, 762, 769, 771; 604/1, 312, 358

[56] References Cited

U.S. PATENT DOCUMENTS

| | | | |
|---|---|---|---|
| 4,246,339 | 1/1981 | Cole et al. | 435/7 |
| 4,418,702 | 12/1983 | Brown et al. | 128/760 |
| 4,580,577 | 4/1986 | O'Brien et al. | 128/760 |
| 4,635,488 | 1/1987 | Kremer . | |
| 4,774,962 | 10/1988 | Hebel et al. | 128/760 |
| 4,834,110 | 5/1989 | Richard | 128/760 |
| 5,008,080 | 4/1991 | Brown, III et al. | 422/56 |
| 5,056,521 | 10/1991 | Parsons et al. | 128/635 |
| 5,103,836 | 4/1992 | Goldstein et al. | 128/760 |
| 5,260,031 | 11/1993 | Seymour | 128/760 |

FOREIGN PATENT DOCUMENTS

0414513A3 2/1991 European Pat. Off. .
WO91/13355 9/1991 PCT Int'l Appl. .

*Primary Examiner*—Max Hindenburg
*Attorney, Agent, or Firm*—Peter J. Dehlinger; Vincent M. Powers

[57] ABSTRACT

A device for obtaining oral fluid containing substances for testing. In one embodiment, the device includes a syringe having a plunger at the end of which an absorbent pad is attached. A test assembly containing the device is also disclosed.

9 Claims, 3 Drawing Sheets

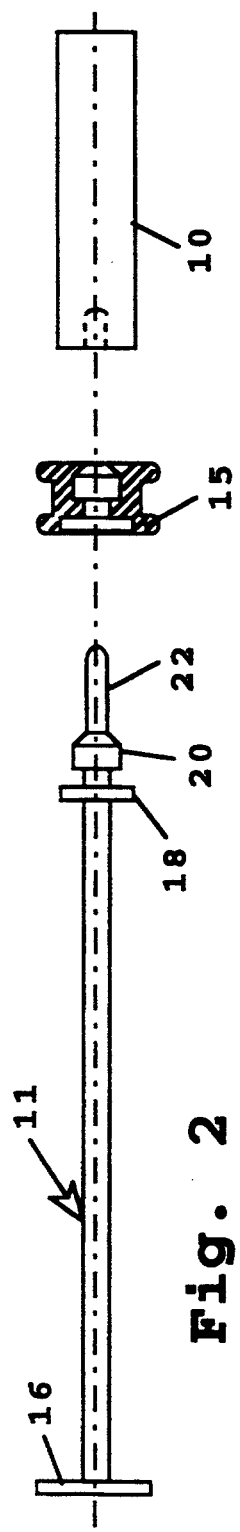
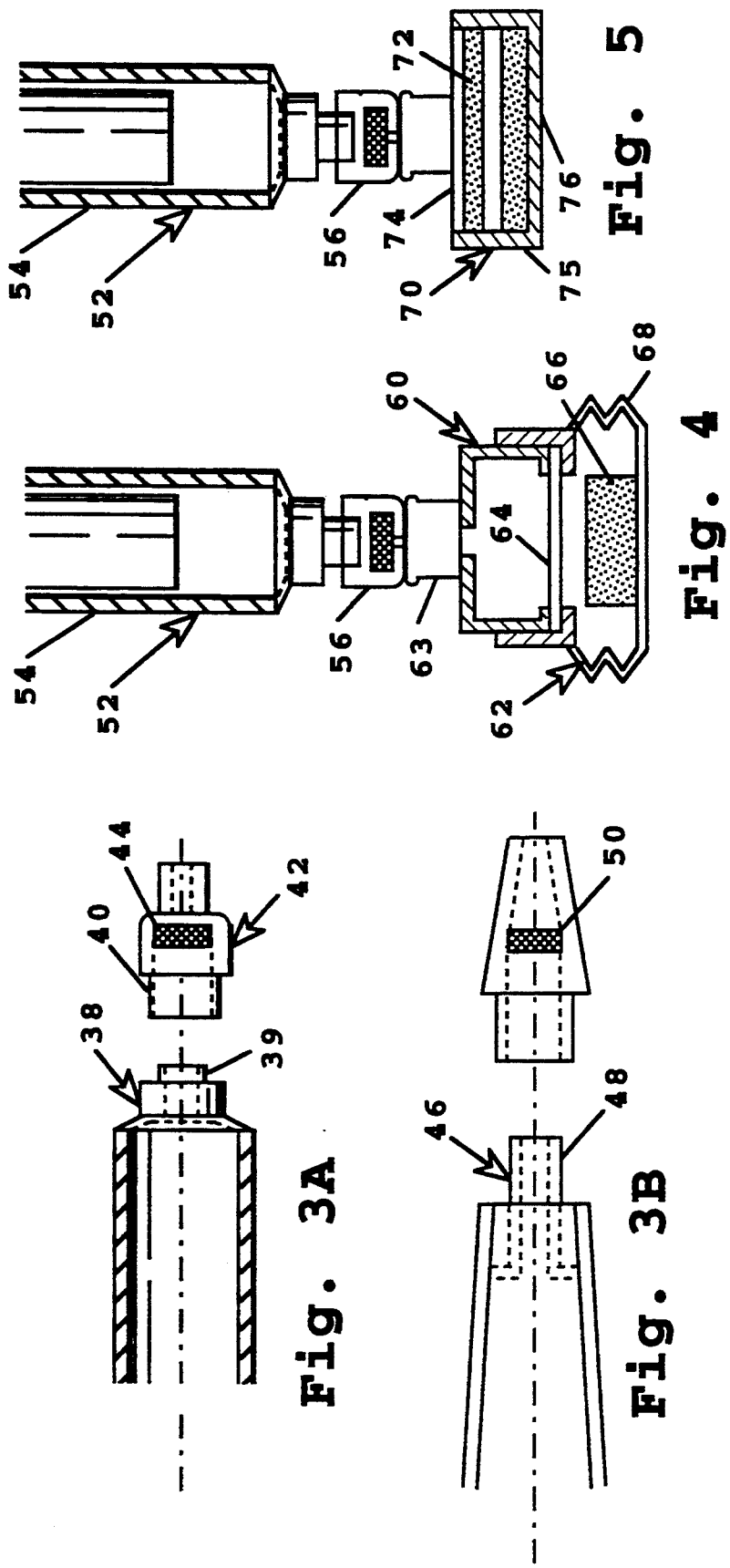

ORAL COLLECTION DEVICE

This application is a continuation-in-part of copending application Ser. No. 07/865,054, Apr. 8, 1992, now abandoned which is a continuation-in-part of Ser. No. 07/641,739, Jan. 15, 1991, now U.S. Pat. No. 5,103,836, which is a continuation-in-part of Ser. No. 07/486,415, Feb. 28, 1992 abandoned, which is a continuation-in-part of Ser. No. 07/410,401, Sep. 21, 1989, now U.S. Pat. No. 5,022,409.

1. FIELD OF THE INVENTION

The present invention relates to devices and methods for obtaining oral fluid for testing.

2. REFERENCES

Parry, J. V., et al., Lancet 2:72–75 (1987).

Thieme, T., et al., J. Clin. Microbiol. 20:1076–1079 (1992a).

Thieme, T., et al., "Oral Fluid Sampling for Determination of HIV-I Antibody Serostatus," Abstract from VIII Int'l. Conf. on AIDS, pg. C328 (1992b).

3. BACKGROUND OF THE INVENTION

A number of analytical procedures and devices are commonly used to test body fluids for the presence of substances of diagnostic value. Blood and urine are the body fluids of choice. An advantage of blood as a test fluid is that analytes are often at relatively high concentrations, and measurements of these concentrations can often provide information about a patient's health. Urine is useful for diagnostic testing when the blood component of interest (e.g., a low molecular weight drug or hormone) is concentrated during urine formation. However, the urine concentration of an analyte does not usually reflect the physiologically active amount of the analyte in blood.

Although saliva is not commonly used as a body fluid in medical diagnosis, numerous studies (Parry, et al.; Thieme, et al., 1992 a,b) have demonstrated that saliva and other types of oral fluid can provide a reliable sample for diagnostic testing involving antibodies or antigens specific for various human or animal pathogens. Oral fluids have also been shown to be useful in measuring the body levels of naturally occurring hormones or therapeutic and other drugs.

One advantage of sampling oral fluid over sampling blood and urine is the convenience of obtaining the sample. A trained phlebotomist is not required, as is the case with blood, nor are special arrangements for privacy-in-collection and custody of the sample required, as is the case with urine. Furthermore, collection of an oral fluid sample obviates the hazard of handling blood-contaminated needles and tubes.

Devices for the collection of oral fluid have been described. U.S. Pat. Nos. 4,418,702 and 4,580,577 show an absorbent pad for absorbing oral fluid, and a barrel-piston arrangement for extracting the fluid from the pad.

U.S. Pat. No. 4,774,962 describes an absorbent pad for absorbing saliva, and a centrifuge tube and tube-insert for removing oral fluid from the pad by centrifugation.

U.S. Pat. No. 5,056,521 describes an apparatus for use in monitoring glucose in oral fluid. The apparatus includes a barrel-piston arrangement having a nonreactive absorbent swab secured to the piston. The barrel and piston are used to squeeze the fluid sample from the swab into a glucose monitoring instrument.

4. SUMMARY OF THE INVENTION

In co-owned U.S. Pat. No. 5,103,836, there is described a novel pad for collecting oral fluid from an individual, as part of an assay for test substances in the fluid. The pad is impregnated with salts which are effective to enhance the recovery of such substances, particularly immunoglobulins, from the oral fluid. Once oral fluid is absorbed into the pad, the fluid may be extracted by centrifugation in a specially designed collection tube. The invention includes, more generally, a device for collecting oral fluid for diagnostic purposes, an impregnated pad of the type just described, and structure for extracting absorbed oral fluid from the pad.

In a particular embodiment of the invention described herein, the structure for extracting absorbed oral fluid from the pad includes a syringe having a barrel, and a plunger to which the pad is attached.

In one preferred embodiment, the syringe further includes a fluid passageway at the outlet end of the barrel, and detection reagent(s) contained in the passageway, effective to be released into the oral fluid when such is expelled from the barrel. The passageway may be defined by a cartridge that is detachably mounted on the barrel.

In a related aspect, the invention includes an assay assembly for use in assaying test substance in the oral fluid. The assembly includes the above-described pad-syringe structure, and a detection unit constructed for receiving oral fluid expelled therefrom. The detection unit includes a solid-support, and a binding agent attached thereto, effective to bind specifically to a test substance in the oral fluid when the oral fluid is expelled from the barrel into the unit. The detection unit may be attachable to the outlet end of the syringe, or may be used as a separate fluid-receiving structure.

The assembly may further include a passageway that connects the barrel of the syringe in fluid communication with the detection unit. The passageway may contain detection reagent(s) effective to be released into the oral fluid when such is expelled from the barrel. Preferably, the detection reagent(s) are effective to react with a test substance in the oral fluid to produce on the support, a detectable signal which is dependent on the concentration of the test substance in the oral fluid.

In one preferred embodiment of the assembly, the solid-support is a permeable membrane and the detection unit further includes an absorbent material that can be brought into contact with the membrane, to draw fluid through the membrane support.

In one configuration, the test substance is an antibody that is diagnostic of infection by a known pathogen. The binding agent can be an antigen that is immunoreactive with the test antibody, in which case the assembly may further include a reporter-labeled reagent effective to bind to the test-substance antibody, when such is bound to the solid-support.

Alternatively, the binding agent can selectively bind human antibodies, in which case the assembly may further include a reporter-labeled antigen that is immunoreactive with the test-substance antibody. One exemplary binding agent for binding the test substance antibody is protein A.

In another configuration, the test substance is an antigen that is diagnostic of infection by a known pathogen. The binding agent can be an antibody that is immunoreactive with the test antigen, in which case, the assembly may further include a reporter-labeled reagent effective to bind to the test substance antigen, with such bound to the solid-support.

In another aspect, the invention includes a solid-support surface for simultaneous assay of both a test substance and a marker substance in an oral-fluid sample, i.e., a substance which gives a positive indication that oral fluid is being tested. The first and second binding agents for binding the test substance and the marker substance, respectively, may be located on at least partially non-overlapping regions of the surface. Preferably the two binding regions form the two bars of a "+" symbol.

These and other objects and features of the invention will become more fully apparent when the following detailed description of the invention is read in conjunction with the accompanying drawings.

BRIEF DESCRIPTION OF THE DRAWINGS

FIG. 2 is an assembly view of the plunger and pad in the FIG. 1 device;

FIG. 3A and 3B show alternative cartridge and syringe barrel embodiments;

FIG. 4 shows a cross-sectional side view of a test assembly according to the present invention;

FIG. 5 shows a cross-sectional side view of another embodiment of a test assembly according to the present invention.

DETAILED DESCRIPTION OF THE INVENTION

A. Oral Fluid Collection Device

Figure 1A:
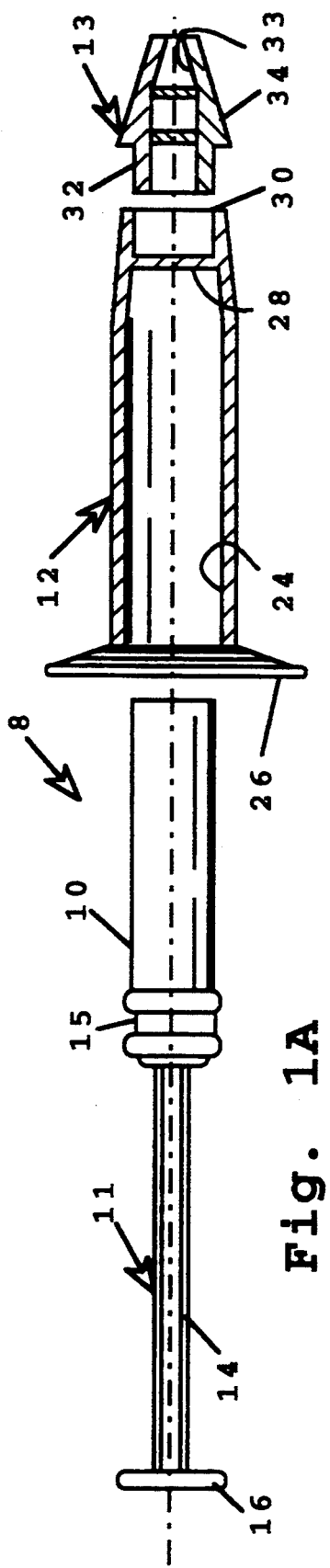
FIGS. 1A and 1B are cross-sectional side views of an oral fluid collection device according to an embodiment of the present invention, shown before (FIG. 1A) and after (FIG. 1B) plunger engagement with a barrel in the device.
Figure 1B:
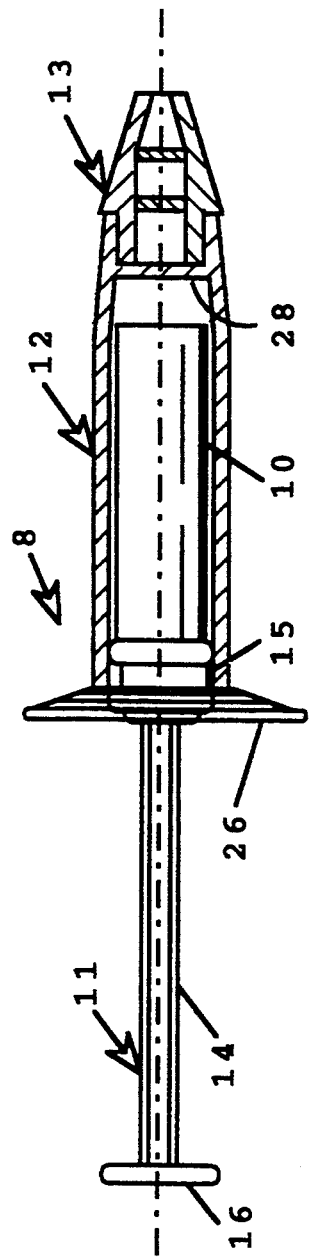

FIGS. 1A and 1B illustrate an oral fluid collection device 8 constructed according to the present invention. The device generally includes an absorbent pad 10, which functions as an oral-fluid collector, a plunger 11 to which the pad is attached, a syringe barrel 12, and in the embodiment shown, a detachable reagent cartridge 13.

Plunger 11 includes a plunger stem 14, a sealing gasket 15 located on the inner end of the plunger, and a thumb tab 16 located on the outer end of the plunger. FIG. 2 shows an assembly view of the plunger and pad. The plunger stem conventionally includes a pair of radial enlargements 18, 20 adjacent its inner end, and terminates in a finger projection 22, as shown. The stem and thumb are preferably formed by injection molding of a suitable polymer, conventionally.

Gasket 15 is a soft rubber or flexible polymer material designed to be received on the plunger, and held in position by enlargements 18, 20, as can be appreciated, with projection 22 extending through the end of the gasket. The diameter of the gasket is such as to form a snug, liquid-tight seal with the interior wall of barrel 12.

Pad 10 is attached to the inner end of plunger 11 by a conventional adhesive, such as the class of silicon rubber adhesives suitable for human oral use. The pad is attached to the stem at contacting surfaces which include the inner face of gasket 15, and the portion of projection 22 which is received within the pad, as can be appreciated from FIG. 2.

The pad can be made of any of a number of absorbent materials suitable for oral use. Preferably, the pad is a thick, absorbent cotton roll or paper, such as commonly used in dental procedures. An example of such a pad is a 1.5 inch No. 2 medium cotton roll distributed by Patterson Dental Co. (Minneapolis, Minn.). Materials such as cellulose, polyurethane, polyester, and rayon are also useful.

According to an important feature of the invention, the pad is impregnated with the salts of a hypertonic solution, in an amount effective to recover a high concentration of test substance, such as immunoglobulin, in the oral fluid. As detailed in co-owned U.S. Pat. No. 5,103,836, which is incorporated herein by reference, the use of a hypertonic solution results in a constant production of immunoglobulin from other sources within the oral cavity, those sources not being completely understood. By using a hypertonic solution, it is possible to gain an increase of as much as 8-16 times for immunoglobulin than by using distilled water.

A hypertonic solution is a salt solution which has an ionic strength exceeding that found in blood. In general, salts used in the preparation of the hypertonic solution of the present invention are present in an amount of from about 1.5% to about 5% by weight, preferably 3.5% by weight.

Salts which can be used in the preparation of the hypertonic solution include alkali met al compounds as well as alkaline earth met al compounds. Preferred salts include sodium chloride, potassium chloride, magnesium sulfate, magnesium chloride and calcium chloride. Sodium chloride is found to be the least toxic, least expensive and most palatable.

The hypertonic solution of the present invention can also include a compound or ingredient for stimulating salivation. The compounds capable of stimulating salivation are found to exhibit a sour taste. These compounds include weak organic acids. Preferred among the weak organic acids are citric acid, ascorbic acid and acetic acid. It is preferred to use citric acid and ascorbic acid at a concentration of between about 0.05% and 0.5% by weight. The preferable range for acetic acid is between about 0.5% and 3.0% by weight.

In order to minimize degradation in a collected specimen, the hypertonic solution of the present invention can include a preservative. Such a preservative can act to inhibit proteolytic enzymatic activity which can be responsible for the destruction of antibody molecules. Compounds contemplated as a preservative include antibacterial agents, anti-fungal agents, bacteriostatic agents, fungistatic agents, and enzyme inhibitors. In a preferred embodiment benzoic acid, sorbic acid or the salts thereof are used as anti-fungal agents. As bacteriostatic agents, salts in high concentration and compounds capable of maintaining the hypertonic solution at low pH are contemplated. Such salts include thimerosal (or merthiolate), phenyl mercuric acetate, phenyl mercuric nitrate and sodium azide. Other preferred preservatives include preservatives which are typically used in medicines and mouthwashes. Examples include ethyl alcohol and chlorhexidine gluconate. Another class of preferred anti-microbial and anti-viral agents are detergents which can be used as topical germicides or in mouthwashes. An example is benzalkonium chloride. It is preferred to use these preservatives in a range of about 0.01% to about 0.2% by weight.

The pad is impregnated with the hypertonic solution by known means. The hypertonic solution of the present invention can be applied to the pad by dipping the pad into the hypertonic solution so that the salts of the solution can be absorbed into and onto the pad, removing the pad from the solution and allowing the pad to dry. Typically, the pad is dipped into the hypertonic solution and about 1 ml of solution is absorbed. Alternatively, the hypertonic solution could be sprayed onto the pad until a sufficient amount, preferably about 1 ml is absorbed. Excess liquid is shaken off and the pad is placed in a forced-air, convection drying oven at 50° C. for 2 hours or, alternatively, in an oven at 80° C. for 6-12 hours in the absence of forced air. After drying, there will be formed a specially treated pad which comprises the salts of the hypertonic solution of the present invention. It is preferred that as preservatives, such salts as benzalkonium chloride, acetyl pyridinium chloride or chlorhexidine gluconate be used in the preparation of the pad.

Most materials from which the pad can be made can non-specifically bind protein. Thus, some immunoglobulins can undesirably bind to the pad and it is desired to block proteins from binding to the pad by using a blocking agent. Non-specific binding is not normally a problem in the collection of blood samples since blood contains its own blocking agent (i.e., human serum albumin).

To reduce non-specific binding in the collection of oral specimens, a blocking agent can be added to the hypertonic solution to be incorporated into the pad. A blocking agent is generally a soluble protein which is used to prevent non-specific binding of another protein to a solid surface. Compounds which can be added as blocking agents include albumin and gelatin, but any water soluble, non-toxic protein can be used as a blocking agent as long as the protein does not adversely affect the assay being used. It is preferred to use bovine gelatin. In general, blocking agents can be added to the hypertonic solution of the present invention at a concentration of between about 0.01% and 0.2% by weight. The contents of the hypertonic solution are then incorporated into the pad as described above.

The preferred solution to be used in the preparation of the pad has the following composition:

| component | conc. (wt. %) |
| --- | --- |
| sodium chloride | 3.5% |
| citric acid | 0.3% |
| sodium benzoate | 0.1% |
| potassium sorbate | 0.1% |
| bovine gelatin | 0.1% |
| distilled water | |
| addition of 0.1N sodium hydroxide to increase Ph to about 6.5 | |

With reference again to FIGS. 1A and 1B, syringe barrel 12 defines an inner wall 24 dimensioned lengthwise to receive the pad and plunger gasket, as shown in FIG. 2A, and in diameter, to snugly receive gasket 15, to form a fluid-tight seal therewith. The barrel has a flanged or radially enlarged opening 26 which facilitates placement of the pad, after oral-fluid-collection, into the barrel. The opposite, inner end of the barrel is provided with a frit 28 which acts as a fluid-permeable filter to allow passage of oral fluid absorbed in the pad to be expelled from the barrel, as the plunger is forced into the barrel. An outlet port 30 at the end of the barrel provides a socket for receiving cartridge 13. In an embodiment of the device which does not include cartridge 13, the outlet end of the barrel may be tapered to a narrow outlet, as in standard syringe construction. The syringe is also referred to herein as means for extracting oral fluid that has been absorbed into the pad.

Exemplary dimensions for the plunger-pad assembly and barrel according to the present invention are as follows. Plunger 11 is about 3 inches in length, including the length of sealing gasket 15, and about 0.12 inches in diameter. Absorbent pad 10 is about 1.5 inches in length and 0.375 inches in diameter. If a soft rubber gasket is used, a gasket diameter of 0.5 inches and a length of about 0.25 inches is appropriate to form a liquid-tight seal in a syringe barrel having an inner diameter of about 0.4375 inches.

Cartridge 13 includes an annular plug 32 which fits snugly into the socket in the barrel, to hold the cartridge firmly in the barrel. An interior passageway 33 through the chamber is provided with a reagent disc 34 impregnated with detection reagent(s) which are released into the oral fluid, preferably as solute components, when oral fluid is expelled through the cartridge. The reagent(s) are for use in detecting selected analyte(s) in the oral fluid, as discussed below. In addition, the reagent(s) may include a blocking agent such as gelatin, milk casein, or bovine serum albumin, suitable for use in certain types of solid-phase assays, also as discussed below. In one embodiment, a reporter-labeled antibody or antigen is dissolved at a concentration of a few mgs/ml in an aqueous solution containing 0.5% gelatin and 30% sucrose (to facilitate solubilization of protein when oral fluid passes through the cartridge). The reagent disk in the cartridge is sandwiched between fluid-permeable frits 35 and 36 in the cartridge chamber.

Additional embodiments for a cartridge and barrel are shown in FIGS. 3A and 3B. For example, as shown in FIG. 3A, a barrel outlet 38 can be a male Luer ™ fitting 39 for attaching a corresponding female fitting 40 in a cartridge 42. The cartridge includes a rigid frit 44 impregnated with detection reagent(s). A similar arrangement is shown in FIG. 3B except that the male Luer ™ fitting 46 of a barrel outlet 48 is recessed in the body of the barrel. FIG. 3B also shows a barrel configuration in which the interior wall of the barrel is tapered on progressing toward its outlet end, to reduce the amount of oral fluid that remains in the barrel when the pad is compressed.

A strip 50 in the cartridge is a wetable reagent strip which, when wetted by oral fluids passing through the barrel, produces a detectable color change in the presence of analyte in the oral fluids. Analytes such as glucose can be detected using known enzymes, such as glucose oxidase coupled with a peroxidase system effective to produce a detectable color change in the presence of $H_2O_2$.

In each of the cartridge embodiments illustrated in FIGS. 1-3, an interior chamber defines a passageway, such as the interior passageway 33 in cartridge 13, which may contain detection reagent(s) or reagent means effective to be released into the oral fluid when such is expelled from the barrel (FIGS. 1 and 2), or effective to mix with oral fluid passing through the passageway (FIG. 3).

Alternatively, the passageway containing the detection reagents may be contained in the outlet end of the barrel, e.g., along the side walls of a barrel outlet, avoiding the need for a separate cartridge.

To collect a substance from the oral cavity with a collection device such as that illustrated in FIGS. 1A and 1B, the plunger-pad assembly is placed in the mouth of the patient such that the pad lies entirely within the mouth. Placement of the pad between the lower cheek and gums facilitates absorption of secretions originating from gingival lymphoid tissue as well as secretions from submucosal lymphoid tissue and salivary gland lymphoid tissue. It is preferable that the specimen be collected by rubbing the pad back and forth between the gums for about ten seconds and then holding the pad in position for between about thirty seconds and two minutes. After the pad has been impregnated with oral fluid, the pad is withdrawn from the mouth, and the plunger-pad assembly is placed in the syringe barrel pad-end-first so that oral fluid can be extracted from the pad.

The oral fluid can be stored for later analysis, preferably in a suitable preservation fluid. Alternatively, the oral fluid can be mixed with detection reagent(s) or expelled directly (without detection of reagents) or after mixing with detection reagents on a solid-phase detection device, as described in Section B below.

Alternatively, the reagent(s) introduced into the oral fluid may be designed for assay of an oral-fluid analyte by a solution-phase homogeneous assay. The assay, for example used in detecting an antigen-specific antibody present in oral fluid, can be based on a variety of homogeneous assay formats, for example based on coupled enzymes, fluorescence quenching, or an EMIT configuration (Gosling, J., Clin Chem, 36(8):1408 (1990). Alternatively, the assay may involve immunoprecipitation of an analyte in the oral fluid, leading to a detectable agglutination product, such as colored microspheres coated with an immunoprecipitin.

From the foregoing, it will be appreciated how various objects and features of the invention are met. The impregnated pad, containing hypertonic-solution salts, has been shown to produce a several-fold enhancement of recovery of test substances, such as immunoglobulins, from oral fluid. The device is convenient for hospital, clinic, or even home use, allowing an oral sample to be collected easily and immediately assayed. The device also reduces the risk of sample contacting the user, since the plunger-pad assembly can be inserted into the syringe barrel following collection of a sample, and disposed of encased in the syringe barrel.

B. Oral Fluid Assay Assembly

In another aspect, the invention includes an assembly for detecting a test substance in oral fluid. The assembly generally includes an absorbent-pad syringe device of the type described above, and a detection unit adapted to receive oral fluid expelled from the absorbent pad. The detection unit has a solid-support contained within the detection unit, and a binding agent attached to the solid-support effective to bind specifically to a test substance in the oral fluid when the oral fluid is expelled from the barrel into the unit. The concentration of analyte, e.g., antigen or immunoglobulin, in the oral fluid is then determined by the amount of analyte bound to the support.

In one embodiment, the assembly includes a passageway, such as described in section A above, that contains detection reagent(s) (a) effective to be released when oral fluid is expelled from the syringe, and (b) includes one or more reagent components needed to produce a detectable solid-phase binding reaction involving analyte binding to the solid-phase surface.

The choice of assay format depends on the nature of the test substance of interest. Such test substances include a variety of immunoreactive analytes, such as drugs or drug metabolites, for example, cocaine or nicotine or metabolites thereof, vital and bacterial antigens, such as hepatitis B surface antigens, immunoglobulins, particularly IgG and IgM, and hormones, such as $\beta$-HCG. Methods for adsorbing or covalently attaching a selected binding agent to the solid support are well known, and include adsorption of biotinylated proteins, such as ovalbumin, to the membrane, with subsequent attachment of the binding agent, in streptavidin-derivatized form, attachment of antibodies to the support through antibodies specific, e.g., against the $F_c$ portion of the antibodies to be bound, and covalent attachment to surface-derivatizable groups on the membrane, using for example, a variety of available bifunctional coupling reagents.

Two embodiments of an assay assembly according to the present invention are shown in FIGS. 4 and 5. In both figures, the lower portion of a syringe collecting device 52, including a syringe 54 and a cartridge 56, are shown. The collecting device has the same construction as that described in Section A above. In the FIG. 4 embodiment, the detection unit, indicated at 60 is attachable to the cartridge for receiving oral fluid expelled from the cartridge. The cartridge may contain detection reagent(s), such as reporter-labeled molecules, which are effective to compete with analyte molecules for binding to the solid support.

Unit 60 generally includes a housing 62 having an inlet port 63 which is attachable to, and in fluid communication with, the outlet side of the cartridge, as shown. Supported within the housing is a solid-phase support, or membrane 64 which is positioned to receive oral fluid expelled from the syringe device. An absorbent pad 66 is suspended below membrane 64 in an accordion-like structure 68 to draw oral fluid through the membrane, when the pad is brought into contact with the lower side of the membrane.

FIG. 5 shows a detection unit 70 having a membrane 72 which can be viewed through a window 74, both supported in a casing 75. An absorbent pad 76 located below the membrane can be brought into contact with the underside of the membrane, to draw fluid through the membrane, by deforming the bottom of the casing.

Although the detection units in the assembly embodiments shown in FIGS. 4 and 5 are attachable to a syringe device, for receiving oral fluid directly from the syringe, the invention also contemplates an assembly in which the detection unit is a separate structure, designed to receive oral fluid, e.g., by application of oral fluid and other detection reagents to the membrane in the unit.

Figure 6A:
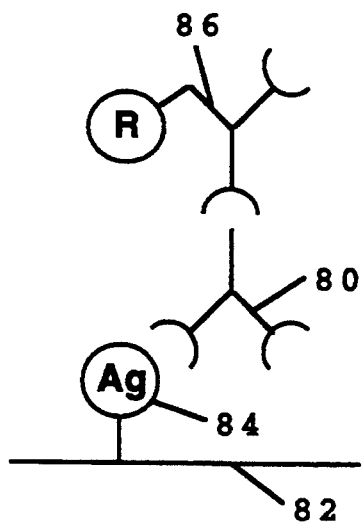
FIG. 6A-6C show exemplary solid-phase formats for detecting a test substance in oral fluid in accordance with the invention.
Figure 6B:
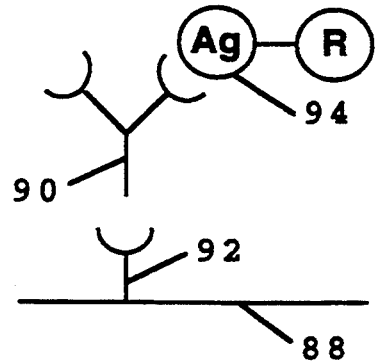
Figure 6C:
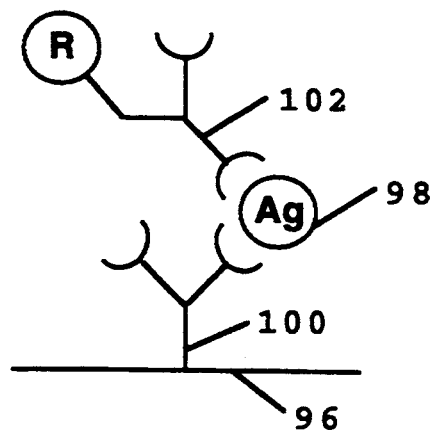

A variety of assay configurations which may be employed in the assembly are illustrated in FIGS. 6A, 6B, and 6C. In FIG. 6A, a test substance 80, an antibody, is captured on a solid-support 82 by immunospecific binding to a support-bound antigen 84. The captured analyte can in turn be detected by a reporter-labeled anti-human antibody 86.

FIG. 6B shows a solid-phase support 88 for detecting a test antibody 90. The analyte antibody is bound to the solid-phase membrane by a binding agent 92, such as protein A or an anti-human immunoglobulin, which is carried on the solid support. Bound analyte antibody can be detected by a reporter-labeled antigen 94 that is immunoreactive with the test antibody.

FIG. 6C shows a solid-support 96 for use in detecting an antigen analyte 98 in the oral fluid. The binding agent in the unit is an antigen-specific antibody 100. Antigen-analyte bound to the support can be detected with a detection reagent which includes a reporter-labeled antibody which is immunoreactive with a second epitopic site on the analyte. Alternatively, the detection reagent may be a reporter-labeled antigen which competes with the analyte antigen for binding to the solid-support binding agent.

Conveniently, the reporter in the above detection reagents is an enzyme, detectable by addition of a suitable substrate, or a fluorescent reporter.

An assay for a test substance in oral fluid can include a simultaneous assay for a marker substance, as described further below. In a typical assay for an oral fluid sample using the solid-support surface of the present invention, the test substance is an antibody that is immunoreactive with an HIV-1 peptide, and the marker substance is transferrin. The solid-support surface includes protein A attached to a first region of the membrane surface, for binding human antibodies, and an anti-transferrin antibody attached to a second region of the membrane surface, effective to capture transferrin. To detect the HIV-1 antibody and transferrin, the assay includes a horseradish peroxidase conjugate of the HIV-1 peptide for which the test HIV-1 antibody is specific, and a horseradish peroxidase conjugate of an anti-transferrin antibody that can bind transferrin irrespective of whether the first anti-transferrin antibody has also bound to the same transferrin molecule. Preferably, the second anti-transferrin antibody is from chicken, since chicken antibodies do not bind to protein A. The reporter-labeled reagents may be impregnated in dried form in a reagent disk which is then placed in a reagent cartridge. The cartridge is then attached to an oral fluid collection device according to the present invention. An oral fluid sample is collected from a patient using the device, and the oral fluid is expressed from the syringe barrel and through the reagent cartridge attached thereto. The reporter-labeled reagents are taken up by and dissolved into the oral fluid as the fluid passes through the cartridge, allowing reaction of the reagents with the respective test and marker substances. The outlet of the cartridge is directed so that the reagent/oral fluid mixture is dispensed onto the solid-support surface. A few drops (~300 μl) of the mixture should be sufficient. The mixture is allowed to remain on the solid-support surface for a time (~5 minutes) sufficient to allow the test substance and the marker substance to bind to the respective detection reagents as well as to the respective binding regions on the solid-support surface. The mixture is then removed from the surface.

In another embodiment, the test substance is a *Helicobacter pylori* antibody, and the reporter-labeled reagent is a reporter-labeled *Helicobacter pylori* antigen.

If the solid-support surface is part of a detection unit according to the assay assembly of the present invention described above, the mixture can be removed by contacting an absorbent pad with the underside of the solid-support to draw the fluid therethrough. Finally, a solution containing hydrogen peroxide and a chromogenic substrate (tetramethylbenzidene, in this example) of horseradish peroxidase is dispensed onto the membrane. Any horseradish peroxidase bound to the solid-support via a test substance or marker substance produces a colored precipitate on the region to which the peroxidase has become bound. The presence of the marker substance and/or test substance is then determined from the pattern that is produced on the solid-support surface.

In one particular aspect of the present invention, an oral fluid sample is simultaneously assayed for a marker substance that is always present in oral fluid, in order to validate the result of the assay for the test substance. Detection of such a marker substance in the sample provides a positive indication that the sample contains oral fluid. Suitable marker substances include transferrin, albumin, ceruloplasmin, and amylase, for example (see "Human Saliva: Clinical Chemistry and Microbiology, Vols. I and II, Tenovuo, J. O., Ed., CRC Press, Boca Raton, Florida (1989)). Marker substances that derive from blood (e.g., albumin and transferrin) are particularly useful when the test substance is also blood-derived (e.g., IgG).

Preferably, both the test substance and the marker substance are assayed using an assay assembly wherein the solid-support includes a flat surface. Preferably, the solid-support is a microporous membrane which can be made of materials such as nitrocellulose or polyvinylidene difluoride, for example. The first and second binding agents for the test substance and the marker substance, respectively, are located on at least partially different (non-overlapping) regions of the surface so that binding of the test and marker substances to the solid-support surface can be distinguished. Methods for binding such binding reagents, both by covalent as well as non-covalent means, are well known in the art. Preferably, the regions are configured to give rise to recognizable patterns that upon viewing can readily convey the result of the assay.

Although the preceding example describes the use of horseradish peroxidase as the reporter, it should be readily appreciated that other enzymes as well as non-enzyme reporters could be used. Moreover, although using identical reporters is convenient, the reporter used to detect the test substance need not be the same as that used to detect the marker substance. In addition, other binding formats can be utilized. For example, in an assay for hepatitis B surface antigen in oral fluid, the binding agent on the solid-support can be a first antibody immunoreactive with the antigen, and the detection reagent can be a reporter-labeled second antibody.

Figure 7:
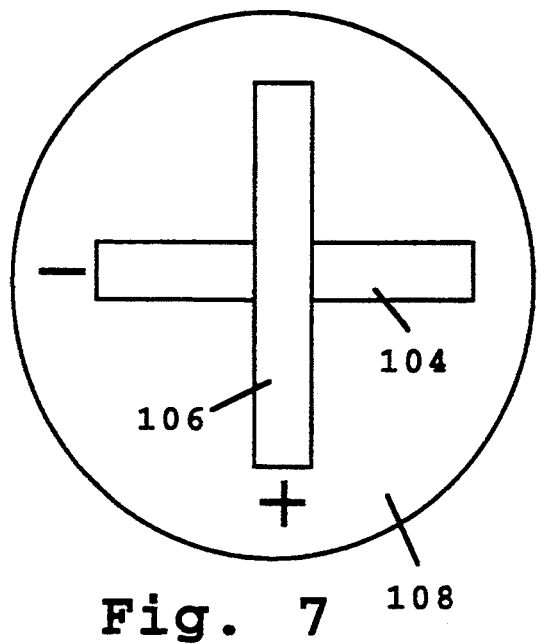
FIG. 7 shows a solid-support surface arrangement for simultaneously assaying a test substance and a marker substance in oral fluid.

One exemplary solid-support surface pattern for conveying the result of the assay is shown in FIG. 7. Bar-shaped regions 104 and 106 in the figure are regions of a solid support 108 which are derivatized or otherwise treated with binding agents which, respectively, are immunospecific or otherwise reactive with a selected oral-fluid marker, such as transferrin, and a selected oral-fluid analyte, such as an antigen-specific analyte. As shown, the two regions are arranged to form a "+" symbol. As can be appreciated, color development in the marker region 104, but not in the analyte region 106 will produce a "—" pattern, indicating that the sample fluid contains the oral-fluid marker, but not the analyte being tested. When such analyte is present, a "+" symbol is observed.

Although the invention has been described with respect to particular embodiments, it will be appreciated that various changes and modifications can be made without departing from the invention.

It is claimed:

1. A device for obtaining oral fluid containing substances for testing comprising:
an absorbent pad impregnated with the salts of a hypertonic solution, said salts being present in the pad in an amount effective to recover a high concentration of such substances from oral fluid, and
means for extracting from the pad oral fluid that has been absorbed into the pad.

2. The device of claim 1, wherein the extracting means includes a syringe composed of a barrel, and a plunger having an inner end to which the pad is attached.

3. The device of claim 2, wherein the test substance is an antibody, and the hypertonic solution includes about 3.5% sodium chloride, about 0.3% citric acid, about 0.1% potassium sorbate, about 0.1% sodium benzoate, and about 0.1% bovine gelatin.

4. The device of claim 2, wherein the barrel has a radially enlarged opening through which the plunger is received.

5. The device of claim 2, which further includes a fluid passageway at the outlet end of the barrel, and which further includes detection reagent means contained in said passageway, effective to be released into the oral fluid when such is expelled from the barrel.

6. The device of claim 5, wherein the fluid passageway is defined by a cartridge that is detachably mounted on the barrel.

7. The device of claim 5, wherein the reagent means includes reagents effective to react with a test substance in the oral fluid to produce a detectable color change.

8. The device of claim 5, wherein the detection reagent means includes reagents effective to react with and agglutinate a test substance in the oral fluid to produce a detectable precipitate.

9. The device of claim 5, which further includes an absorbent strip in fluid communication with the passageway, said strip containing detecting reagents effective to produce a detectable color change when the strip is wetted by the oral fluid, when a test substance is present in the oral fluid.

* * * * *